United States Patent [19]

Iwata et al.

[11] Patent Number: 4,822,615
[45] Date of Patent: Apr. 18, 1989

[54] ANTITHROMBIC RESIN COMPOSITION

[75] Inventors: Kouichi Iwata; Hideo Takahashi, both of Hyogo; Akihiko Isomura, Osaka, all of Japan

[73] Assignee: Sumitomo Electric Industries, Ltd., Osaka, Japan

[21] Appl. No.: 904,833

[22] Filed: Sep. 9, 1986

Related U.S. Application Data

[63] Continuation of Ser. No. 657,437, Oct. 3, 1984, abandoned.

[30] Foreign Application Priority Data

Oct. 3, 1983 [JP] Japan ............................ 58-185599

[51] Int. Cl.$^4$ ........................... A61F 2/00; A61K 9/14; A61K 31/715
[52] U.S. Cl. .................................. 424/423; 424/486; 424/487; 514/56
[58] Field of Search ............... 514/56; 424/423, 486, 424/487

[56] References Cited

U.S. PATENT DOCUMENTS

| | | | |
|---|---|---|---|
| 3,625,745 | 12/1971 | Wright et al. | 117/93.31 |
| 3,673,612 | 7/1972 | Merrill et al. | 514/56 |
| 4,329,383 | 5/1982 | Joh | 514/56 |
| 4,353,996 | 10/1982 | Marconi et al. | 424/83 |
| 4,500,676 | 2/1985 | Balazs et al. | 424/83 |

FOREIGN PATENT DOCUMENTS

| | | |
|---|---|---|
| 2812174 | 9/1978 | Fed. Rep. of Germany . |
| 2142277 | 1/1973 | France . |
| 49-38945 | 11/1974 | Japan ........ 514/56 |

*Primary Examiner*—Frederick E. Waddell
*Attorney, Agent, or Firm*—Sughrue, Mion, Zinn, Macpeak & Seas

[57] ABSTRACT

An antithrombic resin composition comprising is disclosed which comprises synthetic resin having dispersed therein a solution obtained by dissolving an anticoagulant in a solvent. The composition may additionally comprises dispersed therein at least one member of the group consisting of (i) an inorganic substance pulverized to an average particle diameter of not more than 0.1 mm, (ii) a water-absorbing resin powder, and (iii) water-absorbing resin fibers. The resin composition has lasting antithrombic effects and has antithrombic property not merely on the surface of the resin but also throughout the entire resin interior.

8 Claims, No Drawings

ID COMPOSITION

This is a continuation of application Ser. No. 657,437, filed Oct. 3, 1984, now abandoned.

FIELD OF THE INVENTION

This invention relates to a high molecular weight material for medical use, and more particularly to a novel antithrombic resin composition which has uniformly dispersed therein a solution of an antithrombic agent either alone or in combination with a carrier containing the solution.

BACKGROUND OF THE INVENTION

One of the important properties that high molecular weight materials for medical use such as artificial blood vessels, indwelling blood vessel catheters, and artificial dialysis membranes, are required to possess is an antithrombic property which prevents such foreign objects from inducing thrombosis on contact with blood. Generally, blood undergoes coagulation on exposure to an external foreign objects.

In the past, high molecular weight materials for medical use have been made antithrombic by various methods. Among the methods which confer an antithrombic property to high molecular weight materials there is the method comprising binding an anticoagulant to the high molecular weight material. Such method employs, for example, an ionic bond between heparin, a natural anticoagulant, and the cationic group present in the high molecular weight material (Japanese Patent Publication No. 42603/81 and Japanese Patent Application (OPI) No. 194/76. (the term "OPI" as used herein refers to a "published unexamined Japanese Patent Application"). Another method employs a covalent bond with heparin through introduction of an epoxy group into the high molecular weight material (Japanese Patent Application (OPI) No. 162701/82). In these methods, the bonding between heparin and the molecules of high molecular weight material is accomplished by first molding a high molecular weight material possessing a group capable of bonding with heparin in a desired form such as tube or film and subsequently impregnating the molded article with an aqueous heparin solution. Thus they entail complicated procedures and the obtained heparin-bound layers are only on the surface of the high molecular weight materials produced. Thus, the antithrombic property is not imparted to the interior sections of the tube or film. This drawback hinders the actual use of the products in suturation, fusion, and severance. Since the heparin is bound to the high molecular weight material only on the surface thereof, once the heparin on the surface is dissolved out, the high molecular weight material no longer possesses the antithrombic property. Thus, the products obtained by the conventional method have a disadvantage in that they only endure actual use for a relatively short period.

SUMMARY OF THE INVENTION

Accordingly, some objects of the present invention are to provide an antithrombic resin composition which is free from the various disadvantages described above, i.e., which is produced inexpensively without involving any complicated procedure, which manifests lasting antithrombic effects and which acquires the antithrombic property not merely on the surface of the resin but uniformly throughout the entire resin interior.

The above objects have been met by this invention which confers the antithrombic property not by chemical bonding of a high molecular weight material with an anticoagulant as proposed conventionally but, by the uniform dispersion of a solution of an anticoagulant in a molded synthetic resin.

DETAILED DESCRIPTION OF THE INVENTION

In a composition having an anticoagulant in the form of powder simply mixed with a high molecular weight compound, the antithrombic effect of the composition has been confirmed to last for only a very short period since the anticoagulant is incapable of migration within the high molecular weight compound. It has been found by the inventors that when the anticoagulant is dissolved in a suitable solvent and the resulting solution is dispersed in a synthetic resin, the resin composition produced enjoys a lasting antithrombic effect for a very long time because the anticoagulant dissolved out of the surface of the composition upon exposure to blood is replenished by the anticoagulant distributed within the resin composition. It has been also found that the amount of the anticoagulant thus dissolved out of the surface of the resin composition can be controlled by adding to the synthetic resin, in conjunction with the anticoagulant solution, at least one member selected from the group consisting of an inorganic substance pulverized to an average particle diameter of not more than 0.1 mm, a water-absorbing resin powder, and water-absorbing resin fibers, as a carrier retaining the solution.

The synthetic resin employed in the composition of this invention is selected from those synthetic resins fulfilling the requirements of strength, elasticity, corrosion-proofness in living tissues, and inertness to living tissues expected for high molecular weight materials for medical use. Further, the molding temperature should not exceed the decomposition temperature of the anticoagulant. For example, heparin is deactivated at a temperature of not more than 140° C. although it is decomposed at a temperature of not lower than 230° C. Various commercially available plastics, elastomers, and rubbers can be employed. Typical examples include ethylene-α-olefin copolymers as described in, for example, Japanese Patent Application (OPI) No. 82734/83, cyclic esters of caprolactone, ethylene-vinyl acetate copolymers as described in, for example, Japanese Patent Application (OPI) No. 29338/83, and polyisoprene. Of these, ethylene-α-olefin copolymers are preferred. Examples of suitable α-olefins include 1-butene, 1-pentene, 1-hexene, 4-methyl-1-pentene, 1-octene, 1-decene, 1-tetradecene, and 1-octadecene. These monomers can be used alone or in admixture. Of these, those α-olefins having 6 to 18 carbon atoms are preferred since they endow the reulting copolymer with impact strength and resistance to cracks due to stress.

When a mixture of a hydrophobic resin with a hydrophilic resin or a hydrophobic resin having a hydrophilic group graft polymerized thereto is used as the synthetic resin, the ease of migration of the solution of the anticoagulant within the resin is enhanced. Further, the composition, after departure therefrom of the anticoagulant by exudation, converts itself into a pseudointima and enjoys improved adaptability to surrounding living tissues because of the coexistance of a hydrophilic moiety and a hydrophobic moiety.

The expression "hydrophobic resin" as used herein means a resin which lacks a polar group in the molecular configuration, e.g., ethylene-α-olefin copolymers as described in, for example, Japanese Patent Application (OPI) No. 61103/83 and polyisoprene. The expression "hydrophilic resin" as used herein means a resin which incorporates a polar group or a polar atom such as a carboxyl group, an isocyanate group, an amino group, a hydroxyl group, chlorine, bromine and other halogens in the molecular configuration, e.g., polyvinyl alcohol and ethylene-vinyl alcohol copolymers as described in, for example, Japanese Patent Publication No. 42603/81, ethylene-vinyl acetate copolymers as described in, for example, Japanese Patent Publication No. 29338/83, polyamide, and polyacrylonitrile.

Examples of the composite having a hydrophilic group graft polymerized onto a hydrophobic resin are polyolefin type resins having acrylamide, acrylic acid, etc. graft polymerized thereto as described in, for example, Japanese Patent Publication No. 43563/82.

Examples of the anticoagulant which can be used in this invention include heparin, alginic acid sulfate, warfarin and urokinase as described in, for example, U.S. Pat. Nos. 3,766,167 and 4,331,697. In terms of heat stability, antithrombic effect, economy and safety, heparin is preferred.

The solvent for the anticoagulant is only required (a) to possess a boiling point higher than the molding temperature of the resin so as to avoid being vaporized by the heat used for the molding, (b) to produce no noxious effect upon the living tissue, and (c) to enjoy high compatibility with water so as to be readily dissolved out in blood. Water is a good solvent for the anticoagulant. Since water has a low boiling temperature, the use of water limits the freedom in the selection of synthetic resin. As solvents having higher boiling points than water, polyhydric alcohols such as ethylene glycol, propylene glycol, glycerol and polyethylene glycol may be cited. Of these, glycerol is preferred since it dissolves sodium salt of heparin in a high concentration and it is highly safe to living organisms. A solution of an anticoagulant in a polyhydric alcohol can be obtained by preparing a solution of the anticoagulant in water, mixing the solution with a polyhydric alcohol, and thereafter removing water from the resulting mixed solution. Specifically, when an ethylene-α-olefin copolymer (molding temperature 100° C.) is used for the substrate, those solvents having a boiling point of not lower than 150° C. can be used. Glycerol having a boiling point of 290° C. can be advantageously used as the solvent. In this case, a glycerol solution of the sodium salt of heparin in a concentration of up to 40% can be produced by the aforementioned method which uses water as an auxiliary solvent. Sodium salt of heparin dissolves in ethylene glycol and polyethylene glycol in amounts of up to 38% by weight and up to 2% by weight, respectively. It is preferred for sodium salt of heparin to be used in an amount of 1 to 5% by weight based on the total weight of the composition. When this amount is less than 1% by weight exudation or separation of sodium salt of heparin to the surface is insufficient, thus failing to exhibit an antithrombic effect. On the other hand, when the amount of sodium salt of heparin is about 5% by weight excessive exudation occurs and there is a danger of giving side effects to living organism.

Preferably, the amount of a solution of an anticoagulant in the antithrombic resin composition is 5 to 20% by weight based on the total weight of the composition. When this amount is less than 5% by weight, the speed at which the anticoagulant exudes is very low, while the final composition has a strength too low to be used practically when the amount is more than 20%.

By dispersing the solution of anticoagulant in the synthetic resin, the antithrombic property can be conferred throughout the entire depth of the resin. When this solution is added all by itself to the resin, the amount of the solution dispersed and included in the interior of the resin is small. For example, a glycerol solution of an anticoagulant can be included in the synthetic resin up to 5% by weight. When the resin containing the solution in such a small amount is exposed to blood, it suffers from excess departure of the solution in the initial stage of service and fails to provide a lasting antithrombic property.

It has now been found that the dispersion of the solution of anticoagulant in the synthetic resin in conjunction with at least one member of the group consisting of an inorganic substance pulverized to an average particle diameter of not more than 0.1 mm, a water-absorbing resin powder, and a water-absorbing resin fibers solves above-described problem.

If the average particle diameter of the powdered inorganic substance is larger than 0.1 mm, the skin of the surface of the molded article is extremely coarse and the molded article itself has a low capacity for retaining the solution so as to necessitate the addition of a large amount of the powdered inorganic substance. Thus, the molded article is too weak and brittle for practical use. Thus, the average particle diameter of the powdered inorganic substance must be not more than 0.1 mm. Preferably, the average particle diameter of the powdered inorganic substance is 0.1 to 10 μm in view of operability.

Any of ordinary resin fillers such as activated carbon, calcium carbonate, barium sulfate, talc, silica, porous silica, and finely comminuted ceramic can be used as the powdered inorganic substance. Particularly, porous silica or activated carbon which has high liquid-absorbing capacity and large specific surface area is used desirably.

The powdered inorganic substance can be used in an amount of 3 to 50% by weight based on the total weight of the composition.

The average particle diameter of water-absorbing resin powder is not more than 0.1 mm for the same reasons as described for the powdered inorganic substance, and preferably 0.1 to 30 μm for improved dispersibility.

Examples of the water-absorbing resin advantageously usable herein include polyacrylates, acrylate-vinyl alcohol copolymers, polyacrylonitrile hydrolyzate, acrylamide-acrylic acid copolymer, and polyethylene oxide. Of these, acrylate-vinyl alcohol copolymers, which have excellent thermal resistance and durability, are preferred. Such a water-absorbing resin swells by absorbing an aqueous solution of the anticoagulant. For example, a gel not containing a liquid phase whose swelling degree is 77 is formed using 1.3 g of the water-absorbing resin per 100 g of a mixed solution of water-glycerol (1:1 by weight ratio). It is suffice for the water-absorbing resin to absorb water by at least 10 times as much as the weight of the resin. When it is combined with a high boiling solvent compatible with water and then deprived of water, it continues to remain in its swelled form. Thus, it has a high capacity for retaining the solution of anticoagulant and enables the solution of anticoagulant to be dispersed in a large amount within the synthetic resin. Generally, such water-absorbing resins are marketed in powdered forms and they may be put to use without any modification or may be converted into fibers in a conventional manner.

When water-absorbing resin fibers are employed, the solution of anticoagulant is allowed to migrate along the length of the fibers when the resin is exposed to blood. Thus, they are effective in increasing the amount of release of the solution.

Water-absorbing resin fibers having a diameter of not larger than 100 μm, preferably 20 to 50 μm and a length of 6 mm, preferably 0.5 to 3 mm can advantageously used in order to obtain satisfactory dispersion processability and homogeneity.

The water-absorbing resin powder or the water-absorbing resin fibers can be used in an amount of 3 to 15% by weight based on the total weight of the composition.

Hence, it is desirable to use the powdered inorganic substance, water-absorbing resin powder, and water-absorbing resin fibers in proper combinations to suit particular applications.

The fabrication of the composition may be effected by using any ordinary kneader. Examples of the kneader usable herein include a monoaxial extruder, a biaxial extruder, a Banbury mixer, and a roll kneader. The composition melted and kneaded by such a kneader is crushed or cut into particles of a proper size. By the thermoplastic molding methods such as inflation molding, blow molding, extrusion molding, and injection molding, the composition can be molded continuously in the form of film or tube. Such an aftertreatment as the immersion in an aqueous solution of heparin indispensable to the conventional method is no longer required.

The following examples are provided for illustration purposes only and in no way intended to limit the scope of the present invention.

EXAMPLE 1

Powdered sodium salt of heparin was dissolved in water to prepare an aqueous solution of a concentration of 25%. This aqueous solution was stirred with an equal amount of glycerol to produce a homogeneous solution. The resulting solution was vacuum dried at 60° C. for 8 hours to expel water and produce a glycerol solution of 25% sodium salt of heparin. The glycerol solution of sodium salt of heparin and ethylene-α-olefin copolymer (α-olefin: Tafmer ® A-4085 manufactured by Mitsui Petrochemical Industries, Ltd.) were melted and kneaded in a screw type biaxial extruder at 100° C. from about 30 seconds (retention time in the cylinder). The weight proportions of the raw materials by weight were 96% of ethylene-α-olefin copolymer and 4% of the glycerol solution of sodium salt of heparin. The resulting blend was extruded with a T-die extruder at a fabrication temperature of 100° C. to produce a film 0.2 mm in thickness. During the kneading operation and during the extrusion of the film, neither separation of the solution of sodium salt of heparin nor vaporization of glycerol occurred. The produced film had smooth skin.

EXAMPLE 2

A film 0.2 mm in thickness was obtained as in Example 1 except that porous silica having an average particle diameter of 3 microns and BET surface area of 300 m²/g was added in conjunction with the glycerol solution of 25% sodium salt of heparin to the ethylene-α-olefin copolymer. The mixing proportions of the raw materials by weight were 75% of ethylene-α-olefin copolymer, 15% of the glycerol solution of sodium salt of heparin, and 10% of porous silica.

EXAMPLE 3

A film 0.2 mm in thickness was prepared as in Example 1 except that finely pulverized silica having an average particle diameter of 12 millimicrons and BET surface area of 200 m²/g and powdered polyacrylate (Aquakeep ® 10 SH manufactured by Seitetsu Kagaku Co., Ltd.) as a water-absorbing resin were added in conjunction with the glycerol solution of 25% sodium salt of heparin to the ethylene-α-olefin copolymer. The mixing portions of the raw materials by weight were 82% of the ethylene-α-olefin copolymer, 10% of the glycerol solution of sodium salt of heparin, 3% of the finely divided silica, and 5% of the polyacrylate.

EXAMPLE 4

The procedure of Example 3 was repeated except that water-absorbing acrylamide-acrylic acid copolymer (Sumikagel ® F manufactured by Sumitomo Chemical Co., Ltd.) fibers were used in place of the powdered polyacrylate. In this case, the acrylamide-acrylate copolymer was swelled with the aqueous solution of sodium salt of heparin, mixed with glycerol, and thereafter deprived of water. After the removal of water, the copolymer retained its swelled state.

EXAMPLE 5

The procedures of Example 2 was repeated except that a 5:1 (by weight ratio) mixed of ethylene-α-olefin copolymer and polyvinyl alcohol (average molecular weight: 40,000) was used in place of the ethylene-α-olefin copolymer.

COMPARATIVE EXAMPLE 1

Ethylene-α-olefin copolymer and powdered sodium salt of heparin (average particle size: 2 μm) added thereto in a proportion of 3% by weight were melted and kneaded in a screw type biaxial extruder at 100° C. for about 30 seconds (retention time in the cylinder). Then, the resulting blend was extruded through a T-die extruder at a fabrication temperature of 100° C. to prepare a film 0.2 mm in thickness.

From the films produced as described above, 3-cm squares were cut out as test specimens. Each test specimen was repeatedly held in contact with the ACD blood of a dog at 37° C. for 15 minutes to test if thrombosis occurred. ACD blood is a blood to which acid citrate dextrose is added in order to prevent coagulation of the blood during storage. Before use, ACD blood was neutralized by the addition of an aqueous $CaCl_2$ solution. Another test specimen was immersed in 100 ml of physiological saline for 24 hours to determine the amount of heparin dissolved out of the test specimen by isokinetic electrophoresis.

More particularly, the sulfur content (weight ratio) of the sodium heparin was determined in terms of $SO_4^{--}$ ion using isokinetic electrophoresis. Likewise, the sulfur content of the film was also determined. Assuming A and B represent the sulfur contents of the sodium salts of heparin and of the film, respectively and W represents the weight of the film before the immersion in mg, the amount of heparin dissolved out (H in mg) can be obtained according to the following equation:

$$H = \frac{(B_0 - B_1)W}{A} \text{ (mg)}$$

wherein $$A = \frac{\text{Weight of sulfur in the sodium salt of heparin}}{\text{Weight of sodium salt of heparin}}$$

$$B = \frac{\text{Weight of sulfur in the film}}{\text{Weight of the film}}$$

$B_0$: Before the immersion
$B_1$: After the immersion
The results are as shown in Table.

TABLE

| | Number of Contacts with ACD Blood Until Formation of Blood Clot | Amount of Sodium Salt of Heparin Dissolved Out (mg) |
|---|---|---|
| Example 1 | 6 | 1.0 |
| Example 2 | 15 | 1.6 |
| Example 3 | 15 | 1.8 |
| Example 4 | 14 | 2.0 |
| Example 5 | 18 | 1.8 |
| Comparative Example 1 | 2 | 0.2 |

In accordance with this invention, by the direct dispersion of the solution of an anticoagulant in the synthetic resin, the antithrombic property can be conferred uniformly upon the synthetic resin throughout the entire depth thereof. Moreover, by the additional incorporation of a carrier such as an inorganic substance pulverized to an average particle diameter of not more than 0.2 mm, a water-absorbing resin powder, or water-absorbing resin fibers, the amount of the anticoagulant to be included and the amount of the anticoagulant to be dissolved out can be controlled. When the synthetic resin is prepared so as to have a hydrophobic moiety and a hydrophilic moiety combined therein, the resulting resin composition is capable of retaining the antithrombic property intact for a long time. Further, the composition can be molded by the molding method such as extrusion molding or injection molding which enjoys high productivity.

While the invention has been described in detail and with reference to specific embodiment thereof, it will be apparent to one skilled in the art that various changes and modifications can be made therein without departing from the spirit and scope thereof.

What is claimed is:

1. An antithrombic resin composition comprising a synthetic resin which is insoluble in glycerol and has a molding temperature of not more than 140° C. as a mother material having uniformly dispersed therein by melt-kneading (1) a solution obtained by dissolving an anticoagulant which is heparin or a salt thereof in glycerol, and (2) a carrier retaining said solution selected from the group consisting of (i) an inorganic porous powder pulverized to an average particle diameter of not more than 0.1 mm, (ii) said inorganic porous powder admixed with a water-absorbing resin powder, and (iii) said inorganic porous powder admixed with water-absorbing resin fibers.

2. The antithrombic resin composition according to claim 1, wherein said synthetic resin is a mixture of a hydrophobic resin and a hydrophilic resin or a hydrophobic resin having a hydrophilic group graft polymerized thereto.

3. The antithrombic resin composition according to claim 1, wherein said solution is a solution of said anticoagulant which is obtained by removing water from a mixture of an aqueous solution of said anticoagulant with glycerol.

4. The antithrombic resin composition according to claim 1, wherein said resin at the mother material is selected from the group consisting of cyclic esters of caprolactone, ethylene-vinyl acetate copolymer resin and polyisoprene.

5. The antithrombic resin composition according to claim 1, wherein said inorganic substance is selected from the group consisting of activated carbon, calcium carbonate, barium sulfate, talc, silica, porous silica and finely comminuted ceramic.

6. The antithrombic resin composition according to claim 1, wherein said water-absorbing resin is selected from the group consisting of polyacrylates, acrylate-vinyl alcohol copolymers, polyacrylonitrile hydrolyzates, acrylamide-acrylic acid copolymers and polyethylene oxides.

7. The antithrombic resin composition according to claim 1, wherein said resin as the mother material is ethylene-α-olefin copolymer.

8. The antithrombic resin composition according to claim 1, wherein said porous powder is porous silica or activated carbon.

* * * * *